US00PP09729P

United States Patent [19]

Dümmen

[11] Patent Number: Plant 9,729

[45] Date of Patent: Dec. 3, 1996

[54] GERANIUM PLANT NAMED 'HWD CELESTA'

[75] Inventor: Günter Dümmen, Rheinberg-Eversael, Germany

[73] Assignee: Dummen Jungpflanzenkulturen, Rheinberg-Eversael, Germany

[21] Appl. No.: 517,375

[22] Filed: Aug. 21, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of Geranium plant named HWD Celesta, characterized by its semi-double pink flowers; early flowering; large flowers; large number of umbels per plant; and freely branching habit.

1 Drawing Sheet

The present invention relates to a new and distinct cultivar of Geranium plant, botanically known as *Pelargonium× hortorum,* known as the variety Duecelesta, and hereinafter referred to by the cultivar name HWD Celesta.

The new cultivar is a product of a planned breeding program conducted by the inventor in Rheinberg, Germany. The objective of the breeding program was to develop a new semi-double geranium with pink flowers and good weather tolerance.

The new cultivar originated from a cross made by the inventor of the proprietary selection 87-7-7 as the male or pollen parent with the proprietary selection 86-8-5 as the female or seed parent.

The cultivar HWD Celesta was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Geranium are stabilized and reproduced true to type in successive generations of asexual reproduction.

The following traits have been repeatedly observed and are determined to be the unique characteristics of HWD Celesta. These characteristics in combination distinguish HWD Celesta as a new and distinct cultivar:

1. Semi-double pink flowers.
2. Early flowering.
3. Large flowers.
4. Large number of umbels per plant.
5. Freely branching habit.

In comparison to the parent selection 87-7-7, plants of the new Geranium have larger flowers and plants flower earlier. In addition, foliage zonation is less pronounced on the new Geranium compared to the selection 87-7-7. In comparison to the parent selection 86-8-5, plants of the new Geranium have foliage with slight zonation and plants flower later.

The new Impatiens is most similar to the patented cultivars Duerom (U.S. Plant Pat. No. 7,059) and Designer Light Pink (U.S. Plant Pat. No. 8,552). In comparison to the cultivar Duerom, plants of the new Geranium have lighter pink petals, larger flowers, darker green foliage, shorter peduncles, slight zonation, and flower earlier. In comparison to the cultivar Designer Light Pink, plants of the new Geranium have darker pink petals, larger umbels, shorter peduncles, more umbels per plant, and more flowers per umbel.

The accompanying colored photograph illustrates the overall appearance of the new cultivar, showing the colors as true as it is reasonably possible to obtain in colored reproductions of this type. Flower color appears lighter than the actual flower color due to light reflectance. The photograph comprises a top perspective view of a typical potted plant of HWD Celesta with one plant in a 10-cm container.

The cultivar HWD Celesta has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following description, color references are made to the Royal Horticultural Society Colour chart except where general terms of ordinary dictionary significance are used.

Classification:

*Botanical.*—*Pelargonium×hortorum.*

*Commercial.*—Zonal Geranium.

*Cultivar.*—'HWD Celesta'.

Parentage:

*Male parent.*—Proprietary selection 87-7-7.

*Female parent.*—Proprietary selection 86-8-5.

Propagation:

*Type cutting.*—Terminal cuttings.

*Time to initiate roots.*—Summer: 27° C. 21 days; winter: 20° C., 28 days.

Plant description:

*General appearance.*—Rounded; compact to medium plant size; spreading; freely branching.

*Foliage description.*—Arrangement: Generally opposite Shape: Orbicular with rounded tip and cordate base. Size: Length: 6.5 to 7 cm. Width: 7.5 to 8.4 cm. Texture: Velvety; pubescent on upper and under surfaces. Margin: Crenate. Color: Young foliage, upper surface: 144A. Young foliage, under surface: 144A. Mature foliage, upper surface: 146A. Mature foliage, under surface: 146A. Zone, upper surface: 137A, not pronounced. Zone, under surface: None. Veins, upper surface: 144B. Veins, under surface: 144B. Petiole: 144B. Zonation: Width of zone: 1.2 to 1.5 cm. Location of zone: 0.5 cm from margin and 2 to 2.5 cm from petiole. Venation pattern: Palmate. Petiole: Length: 6.5 to 9 cm. Diameter: 1.5 to 2 mm.

*Stem description.*—Internode length: 1 to 1.3cm. Stem color: 144B. Lateral branch number: 11. Lateral branch length: 5.5 to 9 cm.

Flowering description:

*Flowering habit.*—Freely flowering. Flowers arranged in umbels.

*Natural flowering season.*—Year-round.

*Flowers borne.*—Flower buds develop in apical leaf axils. Umbels are displayed above the foliage.

*Quantity of inflorescences.*—Very floriferous; usually 16 open umbels and at least 8 developing umbels per plant at one time.

*Umbels.*—Form: Rounded. Diameter: 12.5 cm. Depth (height): 7 cm.

*Flowers.*—Form: Semi-double. Shape: Rounded. Quantity of flowers per umbel: 26 to 28. Diameter: 4.3 to 4.8 cm. Depth (height): 1.5 cm.

*Petals.*—Shape: Obovate with rounded tip. Arrangement: Rosette, overlapping. Quantity: 5 to 8. Aspect: Flat. Size: Length: 2.3 to 2.7 cm. Width: 2.3 to 2.8 cm. Texture: Satiny, smooth. Margin: Entire. Color: When opening, upper surface: 65A. When opening, under surface: 65D. Upper surface: 73B, 155B, at base. Under surface: 73D. Fading to, upper surface: 155B. Fading to, under surface: 155D.

*Petaloids.*—Shape: Irregular, generally obovate with rounded or clefted tip. Arrangement: Rosette, overlapping. Quantity: 1 to 3. Size: Length: 1 to 2 cm. Width: 1 to 2 cm. Texture: Satiny, smooth. Margin: Generally entire. Color: When opening, upper surface: 65A. When opening, under surface: 65D. Upper surface: 73B, 155B at base. Under surface: 73D. Fading to, upper surface: 155B. Fading to, under surface: 155D.

*Peduncle (umbel stem).*—Angle: Erect. Length: 14 to 15 cm. Pubescence: very fine. Color: 144A.

*Pedicel (individual flower stem).*—Angle: Erect. Length: 3.5 cm. Pubescence: Very fine. Color: 144B.

*Flower bud.*—Shape: Ovoid. Length: 1.6 cm. Diameter: 7 to 8 mm. Color: 66A.

*Sepals.*—Arrangement: Rosette. Quantity: 5. Size: Length: 1 cm. Width: 3 to 3.5 mm. Shape: Acuminate with apiculate tip. Texture: Velvety. Margin: Entire. Color: Upper surface: 144A. Under surface: 144A.

*Reproductive organs.*—Androecium: Stamen number: 9 to 11. Anther size: 1.5 to 2 mm. Anther color: 174A. Pollen color: 34B. Gynoecium: Pistil number: 1. Pistil length: 1 cm. Stigma shape: Decurrent. Stigma color: 64D. Style length: 4 mm. Style color: 64D to 62D, translucent.

*Ploidy level.*—Tetraploid.

Disease resistance: No fungal, bacterial nor viral problems observed.

Seed Development: Seed production is very rarely observed.

It is claimed:

1. A new and distinct cultivar of Geranium plant named HWD Celesta, as illustrated and described.

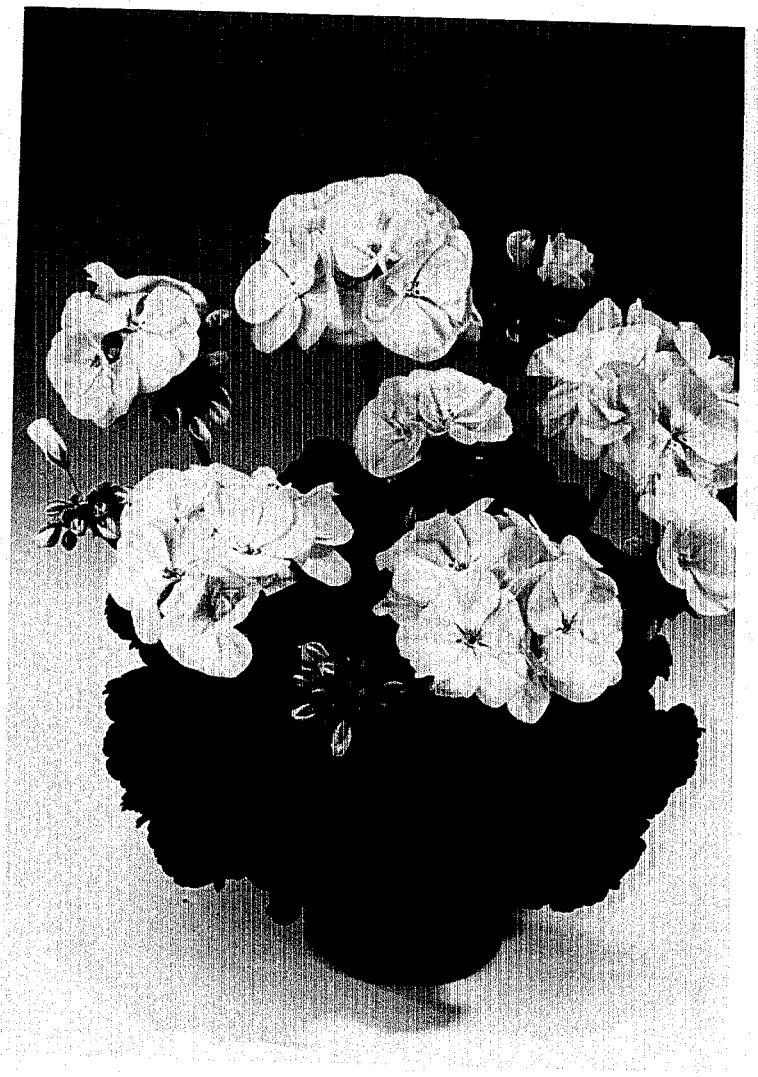

* * * * *